(12) United States Patent
Rhee et al.

(10) Patent No.: US 7,244,591 B2
(45) Date of Patent: *Jul. 17, 2007

(54) YEAST TRANSFORMANT PRODUCING RECOMBINANT HUMAN PARATHYROID HORMONE AND METHOD FOR PRODUCING THE HORMONE

(75) Inventors: Sang Ki Rhee, Seoul (KR); Hyun Ah Kana, Taejeon (KR); Bong Hyun Chung, Taejeon (KR); Su Min Ko, Kyunggi-do (KR)

(73) Assignee: Dong Kook Pharmaceutical Co., Ltd., Seoul (KR)

( * ) Notice: Subject to any disclaimer, the term of this patent is extended or adjusted under 35 U.S.C. 154(b) by 557 days.

This patent is subject to a terminal disclaimer.

(21) Appl. No.: 10/363,329

(22) PCT Filed: Aug. 27, 2001

(86) PCT No.: PCT/KR01/01447

§ 371 (c)(1),
(2), (4) Date: Aug. 14, 2003

(87) PCT Pub. No.: WO02/18570

PCT Pub. Date: Mar. 7, 2002

(65) Prior Publication Data

US 2004/0029252 A1    Feb. 12, 2004

(30) Foreign Application Priority Data

Aug. 31, 2000    (KR) .......................... 2000/0051267

(51) Int. Cl.
| | |
|---|---|
| C12N 15/16 | (2006.01) |
| C12N 1/19 | (2006.01) |
| C12N 15/81 | (2006.01) |
| C07K 14/635 | (2006.01) |

(52) U.S. Cl. ............................... 435/69.4; 435/254.11; 435/320.1; 435/471; 435/942; 530/300; 536/23.51

(58) Field of Classification Search ..................... None
See application file for complete search history.

(56) References Cited

FOREIGN PATENT DOCUMENTS

| KR | 100246932 B1 | 12/1999 |
|---|---|---|
| WO | WO 99/37758 A2 | 7/1999 |

OTHER PUBLICATIONS

Alani et al. A method for gene disruption that allows repeated use of URA3 selection in the construction of multiply disrupted yeast strains. Genetics. Aug. 1987;116(4):541-5.*
Faber et al. Highly-efficient electrotransformation of the yeast *Hansenula polymorpha*. Curr Genet. Apr. 1994;25(4):305-10.*
Choi et al. (1999) "Endoproteolytic processing of human parathyroid hormone in *Saccharomyces cerevisiae* mutants lacking genes encoding the yap3, mkc7 and kex2 endoproteases," J. Microbiol. Biotechnol. 9(5):679-682.
Choi et al. (2000) "Improvement of intact human lipocortin-1 production in *Saccharomyces cerevisiae* by inhibiting proteolysis," J. Biosci Bioeng 89(1):77-80.
Chung et al. (1998) "Simple approach to reducing proteolysis during secretary production of human parathyroid hormone in *Saccharomyces cerevisiae*,"Biotechnol. Bioeng 57:245-249, published by John Wiley & Sons, Inc.
Gabrielsen et al. (1990) "Efficient secretion of human parathyroid hormone by *Saccharomyces cerevisiae*," Gene 90:255-262.
Kang et al. (1998) "Efficient production of intact human parathyroid hormone in a *Saccharomyces cerevisiae* mutant deficient in yeast aspartic protease 3 (yap3)," App. Microbiol. Biotechnol. 50:187-192.
Kang et al. (1998) "Expression and secretion of human serum albumin in the yeast *Saccharomyces cerevisiae*," J. Microbiol. Biotechnol. 8(1):42-48.
Kang et al. (2000) "Proteolytic stability of recombinant human serum albumin secreted in the yeast *Saccharomyces cerevisiae*," Appl. Microbiol. Biotechnol. 53:575-582.
Komano et al. (1995) "Shared functions in vivo of a glycosyl-phosphatidylinositol-linked aspartyl protease, Mkc7, and the proprotein processing protease kex2 in yeast," PNAS USA 92:10752-10756.
Olsen et al. (1999) "Identification and characterization of *Saccharomyces cerevisiae* yapsin 3, a new member of the yapsin family of aspartic proteases encoded by the YPS3 gene," Biochem. J. 339:407-411.
Reppe et al. (1991) "Characterization of a K26Q site-directed mutant of human parathyroid hormone expressed in yeast," J. Biol. Chem. 266(22):14198-14201.
Rian et al. (1993) "Synthesis of human parathyroid-hormone-related protein (1-141) in *Saccharomyces cerevisiae*: a correct amino-terminal processing vital for the hormone's biological activity is obtained by an ubiquitin fusion protein approach," Eur. J. Biochem. 213:641-648.
Song et al. (1999) "Overproduction of human parathyroid hormone by fed-batch culture of a *Saccharomyces cerevisiae* mutant lacking yeast aspartic protease 3," Process Biochem. 35:503-508.
Vad et al. (1998) "High-level production of human parathyroid hormone (hPTH) by induced expression in *Saccharomyces cerevisiae*," Protein Expression and Purification 13:396-402.
Engel-Mitani, M. et al. 2000 "Yield improvement of heterologous peptides expressed in yps 1-disrupted *Saccharomyces cerevisiae* strains" *Enz. Microb. Technol.* 26:671-677.
Copley, K et al. 1998 "Expression, processing and secretion of a proteolytically-sensitive insect diuretic hormone by *Saccharomyces cerevisiae* requires the use of a yeast strain lacking genes encoding the Yap3 and Mkc7 endoproteases found in the secretory pathway" *Biochem. J.* 338:1333-1340.

\* cited by examiner

*Primary Examiner*—David Romeo
(74) *Attorney, Agent, or Firm*—Knobbe, Martens, Olson & Bear, LLP (57) ABSTRACT

Novel *Saccharomyces Cerevisiae* mutant strains are provided for producing human parathyroid hormone. The novel strains acre genetically disrupted in at least one of the genes encoding the yapsin family of proteases Yapsin 1, Yapsin 2 and Yapsin 3 and harbor a human parathyroid hormone gene in their genomes. Culturing the novel strains results in the secretion of intact hPTH into culture media at high yield.

7 Claims, 5 Drawing Sheets

YEAST TRANSFORMANT PRODUCING RECOMBINANT HUMAN PARATHYROID HORMONE AND METHOD FOR PRODUCING THE HORMONE

RELATED APPLICATIONS

This is the U.S. National Phase under 35 U.S.C. §371 of International Application PCT/KR01/01447, filed Aug. 27, 2001, designating the U.S. and published in English, which claims priority to a Korean patent application No. 2000-0051267, filed Aug. 31, 2000, both of which are incorporated herein in their entireties.

BACKGROUND OF THE INVENTION

1. Field of the Invention

The present invention relates to the production of human parathyroid hormone (hereinafter referred to as "hPTH"). More particularly, the present invention relates to the use of Saccharomyces cerevisiae mutant strains which are genetically disrupted in at least one of the yapsin family of aspartic proteases YPS1, YPS2 and YPS3 and transformed with an expression vector anchoring a hPTH gene, in producing the hormone.

2. Description of the Prior Art hPTH is a peptide consisting of 84 amino acid residues, produced by the parathyroid gland. hPTH maintains calcium homeostasis in the kidneys and bones, having the physiological function of promoting calcium metabolism and osteogenesis. In the U.S.A. and the Europe, estrogen or calcitonin have been predominantly used as therapeutics for osteoporosis, but are found to be obstructive of bone absorption. Accordingly, leading pharmaceutical companies of the world are intensively and extensively studying hPTH for the development of therapeutics for osteoporosis by taking advantage of the ability of hPTH to promote osteogenesis. Particularly, more earnest attention is paid to the prophylaxis and treatment of osteoporosis as modern society becomes an aging society. For above reasons, active research is now being directed to the development of biotechnology methods for the mass production of hPTH, which is expected to be a promising therapeutic substitutive for conventional therapeutics for osteoporosis.

For example, various attempts have been made to develop methods for mass-producing recombinant hPTH by using E. coli as a host cell because the prokaryotic bacteria shows relatively high expression efficiency. However, there is a great difficulty in refolding and purifying the recombinant proteins produced from E. coli. In contrast, yeast, a single cell eukaryote, has the advantage of expressing and secreting properly folded- and thus active-proteins because it is very similar to higher species in the gene transcription and translation systems, and its protein-secretion system. Additionally, yeast is advantageous as a host for producing proteins of interest in that yeast secretes few extracellular proteins making it easy to recover and purify exogenous proteins. Further, the yeast Saccharomyces cerevisiae is a GRAS (generally recognized as safe) microorganism that is not pathogenic to the body and does not produce endotoxins. With the anticipation of being very useful as a producer of medicinal recombinant hPTH, Saccharomyces cerevisiae has been studied in developing hPTH expression systems. In spite of its various advantage as an expression host for the production of recombinant hPTH, Saccharomyces cerevisiae is not industrially utilized as such a host because the extracellularly secreted recombinant hPTH is degraded by endogenous proteolytic enzymes of the yeast's own, so that only a small amount of the intact molecule of hPTH can be recovered (Gabrielsen et al., Gene 90, 255(1990)).

In the last decade, extensive studies have been made for solving the proteolysis problem of recombinant hPTH. For instance, based on the finding that hPTH is cleaved between Arg-25 and Lys-26, which is identical to the recognition site of KEX2, a protease present in yeast Golgi bodies, a substitution mutant of hPTH, which has glutamine at position 26 of its amino acid sequence instead of lysine, was made with the aim of preventing the proteolysis by KEX2, which is a putative protease to cleave hPTH (Reppe et al., J. Biol. Chem. 266, 14198 (1991)). Using gene recombination technology, an hPTH-related protein was directly ligated to the 3'-end of the yeast ubiquitin gene to produce a non-cleavable hPTH-related protein (Rian et al., Eur. J. Biochem., 213, 641 (1993)). However, if protein mutants are medicinally used, there are required stringent tests to obtain permission for their medicinal use, because they are generally recognized as new medicines. When using gene fusion technology, it is necessary to remove the fusion site by expected digestion because proteins of interest may be produced at relatively yields owing to the presence of the fusion site.

As a result of the research for the prevention of hPTH degradation without resorting to hPTH protein mutants or fusions, the present inventors developed a method in which hPTH cleavage can be prevented to a significant extent simply by adding L-arginine at high concentrations to the culture media (Chung and Park, Biotechnol. Bioeng. 57, 245 (1998)). The fact that hPTH cleavage is prevented to a significant extent by the presence of L-arginine in the culture media indicates that hPTH cleavage is performed mainly by extracellular proteases rather than by the intracellular protease Kex2p. From this finding, the present inventors inferred that Yap3p (yeast aspartic protease 3), which, like KEX2, is able to cleave the C-terminal or middle sites of basic single or couple amino acids, and binds to the cytoplasmic membrane of yeast, is practically responsible for the cleavage of the hPTH secreted into yeast culture media. On the basis of this inference, the present inventors made a YAP3 gene-disrupted yeast strain (yap3Δ), and constructed an hPTH production system by use of the yeast mutant. Upon culturing in flasks, the hPTH production system was found to prevent the cleavage of hPTH at an efficiency of as high as 80%, thus producing the intact molecule of hPTH at high yield (Kang et al., Appl. Microbiol. Biotechnol., 50, 187 (1998); Korean Pat. No. 0246932, yielded Dec. 8, 1999). Though exhibiting far higher hPTH productivity than the wild type strain, the yap3Δ mutant was observed to allow hPTH to be cleaved to a significant extent in the late stage of the high-concentration culturing (Song and Chung, Process Biochem 35, 503 (2000)), which indicates that hPTH is cleaved not by Yap3p, but by other proteases in the late culture stage. Saccharomyces cerevisiae is reported to have the aspartic protease MKc7p, which is very similar in structure and function to Yap3p (Komano and Fuller, Proc Natl Acad Sci, USA, 92, 10752 (1995)). The present inventors created a yeast mutant in which both of the genes are disrupted (yap3Δ/mkc7Δ) for use in the observation of the influence of the enzymes on the hPTH cleavage at the terminal culture stage. However, no significant differences were found between the mutants yap3Δ and yap3Δ/mkc7Δ (Choi, et al., J. Microbiol Biotechnol 9, 679 (1999)). These results demonstrated that the MKc7p protease, through having high homology with Yap3p (53% homology) and being involved in the processing of pro-α-mating factor in the absence of Kex2p, is not greatly responsible for hPTH cleavage.

Through the analysis of the recently disclosed genome information about *Saccharomyces cerevisiae*, a search was made for genes homologous to YAP3 (recently renamed YPS1), resulting in the finding that three novel genes coding for unknown aspartic proteases, in addition to PEP4 and BAR1, are present (Olsen et al., Biochem. J. 339, 407 (1999)). Assumed to encode new members of the yapsin family of aspartic proteases, like YPS1 and YPS2, the three novel genes were named YPS3, YPS6 and YPS7, respectively. YPS3 was found to have 50% homology with both of YPS1 and YPS2, while 35% and 25% homology was found between YPS6 and BAR1 and between YPS7 and PEP4, respectively. From the homology between YPS3 and YPS1, the present inventors drew the deduction that the hPTH cleavage occurring at the terminal culture stage of the yps1Δ (previous yap3Δ) strain might be performed by yapsin 3.

SUMMARY OF THE INVENTION

With the background in mind, the present invention has an object of providing a protein expression system, which can produce hPTH at high yield.

It is another object of the present invention to provide a method for producing hPTH at high yield.

Knowledge of the posttranslational modification of hPTH allows modification and adaptation leading to the present invention.

As a result of intensive and thorough research on the biological production of hPTH, the present inventors found that the disruption of yapsin genes results in a surprising decrease in the endogenous degradation of recombinant hPTH in *Saccharomyces cerevisiae*.

In accordance with an aspect of the present invention, there is provided a *Saccharomyces cerevisiae* mutant strain in which both of YPS1 and YPS3 genes or all of YPS1, YPS2 and YPS3 genes are disrupted.

In accordance with another aspect of the present invention, there is provided a method for producing hPTH by using the *Saccharomyces cerevisiae* mutant strain as a producer.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The present invention pertains to a method for producing recombinant hPTH from a yeast host which is unable to produce at least one of the yapsin family of proteases YPS1, YPS2 and YPS3.

Showing exoprotease activity to cleave residues from the C- or N-termini of hPTH, the protease Yapsin 1 (hereinafter referred to as "YPS1"), Yapsin 2 (hereinafter referred to as "YPS2) or Yapsin 3 (hereinafter referred to as "YPS3") makes it difficult to produce the intact molecule of hPTH in yeast host. Accordingly, the present invention comprises a method for producing the intact molecule of hPTH at a high yield by using as a host cell a yeast mutant which is unable to express at least one of the three proteases YPS1, YPS2 and YPS3.

It is believed that YPS1 and YPS2 exert their enzymatic activity mostly at the early culture stage of transformants for producing hPTH, while YPS3 cleaves hPTH mainly at the late culture stage. In the case of the yps1Δ strain in which the YPS1 gene is disabled, hPTH can be obtained at a high yield in the early culture stage because of the lacking of YPS1, but at a poor yield in the late culture stage owing to the inevitable proteolytic activity of YPS3.

Accordingly, in order to improve the production yield of hPTH throughout the culturing of a yeast host, a mutant defective preferably in both YPS1 and YPS3 (yps1Δ/yps3Δ), and more preferably in all of YPS1, YPS2 and YPS3 (yps1Δ/yps2Δ/yps3Δ) is used as the host.

Deletion of the proteases can be carried out by disrupting at least one gene selected from the group consisting of YPS1, YPS2 and YPS3 by use of an enzyme selection marker.

The yeast selection marker is not particularly limited, but is preferably a one that can pop-out. In a preferred embodiment of the present invention, a URA3 selection marker is provided in a form of a cassette. The pop-out cassette containing a yeast selection marker has gene fragments coding for N- and C-terminal sites of YPS1, YPS2 and YPS3 at its both ends such that the target genes contained in the genome of yeast, i.e., yps1, yps2 and yps3, can be disrupted by a homology recombination method. Any selection marker may be used if it is able to select the yeast which harbors the cassette in its genome. Herein, the mutant yps3Δ in which the yps3 gene is disrupted by a URA3 selection marker is denoted by yps3::URA3.

In accordance with the present invention, an hPTH gene is carried into yeast by an expression vector. Accordingly, the present invention pertains to a recombinant expression vector to which an hPTH gene is inserted. The expression vector useful in the present invention has means for expressing a gene in yeast and means for controlling the expression. Vector selection and recombinant vector construction are obvious to those who are skilled in the art and details thereof will be described in the following examples.

In another aspect, the present invention pertains to a transformant prepared from the yps1Δ/yps3Δ or yps1Δ/yps2Δ/yps3Δ yeast mutant with the recombinant expression vector.

In a preferred embodiment of the present invention, the recombinant vector pG10-hPTH 1 is transformed into Suecharomyces cerevisiae mutants (ypsIΔ/yps3Δ and yps1Δ/yps2Δ/yps3Δ) to create transformants SLH16/pG10-hPTH and SLH18/pG10-hPTH, which were deposited in the Korean Collection for Type Culture of Korea Research Institute of Bioscience and Biotechnology (KRIBB) (#52, Oun-dong, Yusong-ku, Taeion 305-333, Republic of Korea) with accession Nos. KCTC 0815BP and KCTC 0816BP, respectively, on Jul. 6, 2000. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by KRIBB under the terms of the Budapest Treaty, and subject to an agreement between Applicant and KRIBB which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

A better understanding of the present invention may be obtained in light of the following examples which are set forth to illustrate, but are not to be construed to limit the present invention.

Experimental Strain and Plasmid

For the expression of hPTH in *Saccharomyces cerevisiae*, there was employed the plasmid pG10-hPTH1, which contains an hPTH expression cassette composed of GAL10 promoter::ppL::hPTHdb?::GAL7 terminator (Chung and Park, Biotechnol. Bioeng. 57, 245 (1998)). A pop-out URA3 selection marker (URA3::tc5) cassette was prepared from a 1.8 kb BamHI fragment derived from pTcUR3 (Kang et al., Appl. Microbiol. Biotechnol., 53, 575-582 (2000)). *Saccharomyces cerevisiae* 2805 and *Saccharomyces cerevisiae* L3262a were used as parental cells for preparing YPS3-deleted mutants (Kang et al., J. Microbiol. Biotechnol., 8, 42-48 (1998)). Also, the cells used in the present invention were the yeast strains SLH11 (Kang et al., Appl. Micribiol. Biotechnol., 59, 187 (1998)), SLH12 and SLH14 (Choi et al., J. Biosci. Bioengin., 89, 77 (2000)), which are defective in the YPS1 gene (previously YAP3), the YPS2 gene (previously MKC7), or both of them. Genetic characteristics of the yeast strains are summarized in Table 1, below.

TABLE 1

Saccharomyces cerevisiae Strains Used in the Invention

| Strain | Description/Genotype |
|---|---|
| 2805 | a parental strain (MATα pep4::His3 prb-Δ1.6R can1 his3-20 ura3-52) |
| S28Y3 | a yps1-disrupatant of 2805 (MATα pep4::His3 prb-Δ1.6R can1 his3-20 ura3-52 yps1::tc5) |
| L3262 | a parental strain (MATa ura3-52 leu2-3, 112 his4-34) |
| SLH11 | a yps1-disruptant of L3262 (MATa ura3-52 leu2-3, 112 his4-34 yps1::LEU2) |
| SLH12 | a yps2-disruptant of L3262 (MATa ura3-52 leu2-3, 112 his4-34 yps2::LEU2) |
| SLH14 | a yps3-disruptant of L3262 (MATa ura3-52 leu2-3, 112 his4-34 yps1::HIS4 yps2::LEU2) |

Medium Composition and Culture Condition

When transforming yeast strains with a URA3 cassette for disrupting the YPS3 gene or with the expression vector pG10-hPTH1, the synthetic medium SC-URA which was deficient in uracil only was used. To recover the URA selection marker from the obtained yps3:: URA3 mutant, a 5-FOA (5-fluorotate) medium was employed (Adams et al., Methods in yeast genetics. Cold Spring Harbor Laboratory Press, 1997). For use in the induction of hPTH expression under the control of the GAL 10 promoter, cultures were grown for 48 hours on YPDG media (yeast extract 1%, Bacto peptone 2%, glucose 1%, galactose 1%).

EXAMPLE 1

Establishment of YPS3 Gene-Disrupted Yeast Mutant

Figure 1:
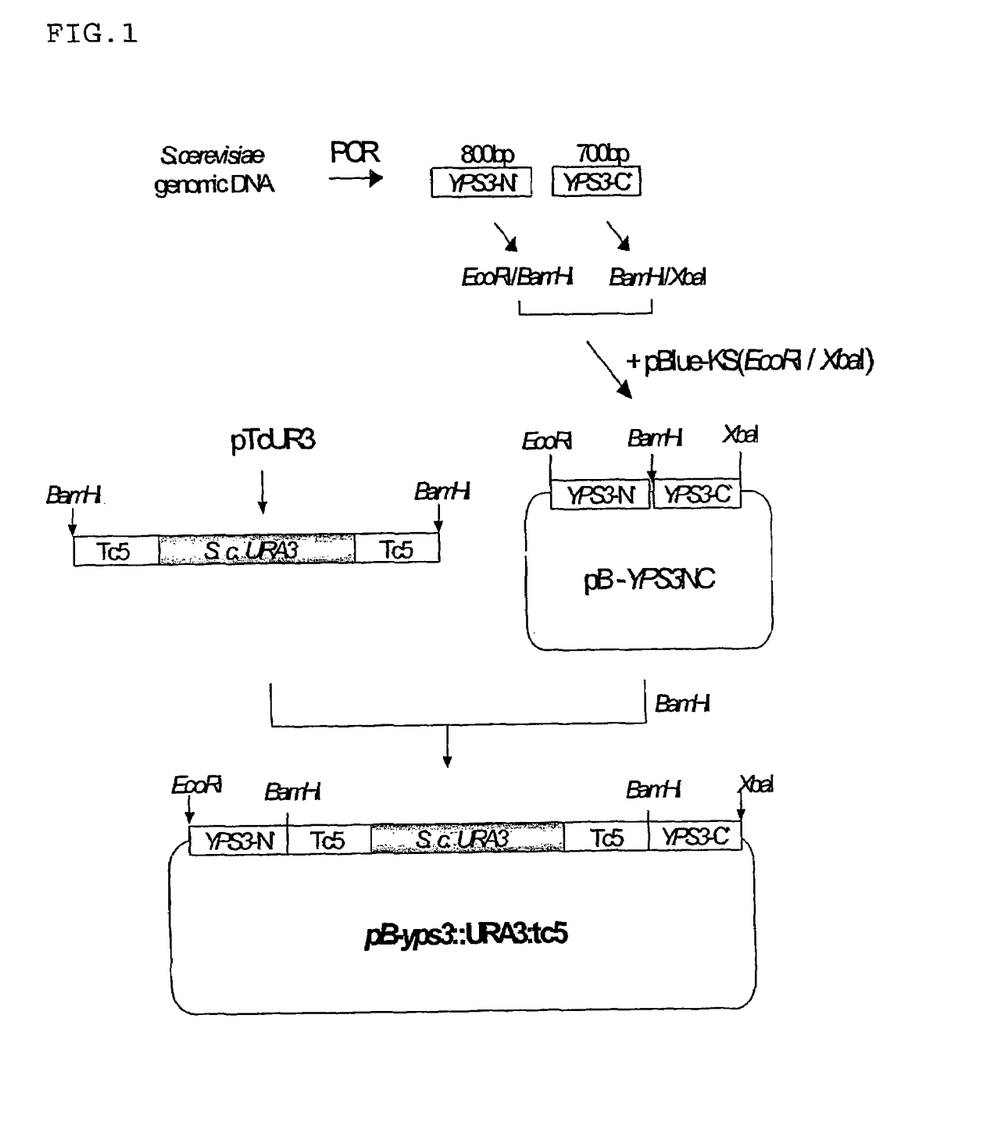
FIG. 1 is a diagram showing a process of constructing a cassette for disrupting the YPS3 gene by use of a pop-out URA3 selection marker.

The construction of a recombinant vector containing a URA3 cassette for use in disrupting the YPS3 gene is illustrated in FIG. 1.

N- and C-terminal fragments of YPS3 gene necessary for the homology recombination leading to the disruption of the YPS3 gene were produced by PCR (polymerase chain reaction) using two pairs of primers, which were synthesized on the basis of the YPS3 base sequence of *Saccharomyces cerevisiae*, registered in GenBank. For the convenience of gene manipulation later, a set of primers (5'-GACGAATTC-CAGAAACGTCTGAGTGGAG-3' (SEQ ID NO: 1) and 5'-GCAGGATCCGTACTCTACCGAATGCCG-3' (SEQ ID NO: 2)) for amplifying the N-terminal fragment were designed to have recognition sites of EcoRI and BamHI at their respective 5'-terminal sites (underlined parts) while restriction sites of BamHI and XbaI were introduced into 5'-terminal sites of a set of primers (5'-CGCGGATCCCTAT-GCAGACCAGTGTGG-3' (SEQ ID NO: 3) and 5'-CGCTCTAGACTGCATGCAAGGTCTGAC-3' (SEQ ID NO: 4)) for the amplification of the C-terminal fragment (underlined parts). The PCR was carried out in a thermal cycler, such as that manufactured by Perkin Elmer, identified as "GeneAmp PCR 24001", with 25 thermal cycles, each consisting of 95° C./30 sec for denaturing, 55° C./30 sec for annealing, and 72° C./30 sec for extending, so as to produce a 800 bp and a 700 bp-DNA fragment encoding an N-terminal and a C-terminal region of the YPS3 gene region, respectively, from the genomic DNA of *Saccharomyces cerevisiae*. The PCR products, that is, the YPS3 N-terminal and C-terminal fragments, were double digested with restriction enzymes EcoRI/BamHI and BamHI/XbaI, respectively, followed by ligating the two restriction enzyme digests together into the pBluescript II KS(+) vector (Stratagen) which was previously treated with EcoRI/XbaI. To the BamHI recognition site located between the two terminal fragments of the resulting recombinant vector pB-YPS3NC, a URA3 popout selection marker was introduced, so as to construct the 15 pB-yps3:: URA3: tc5 vector for use in disrupting the YPS3 gene.

Figure 2:
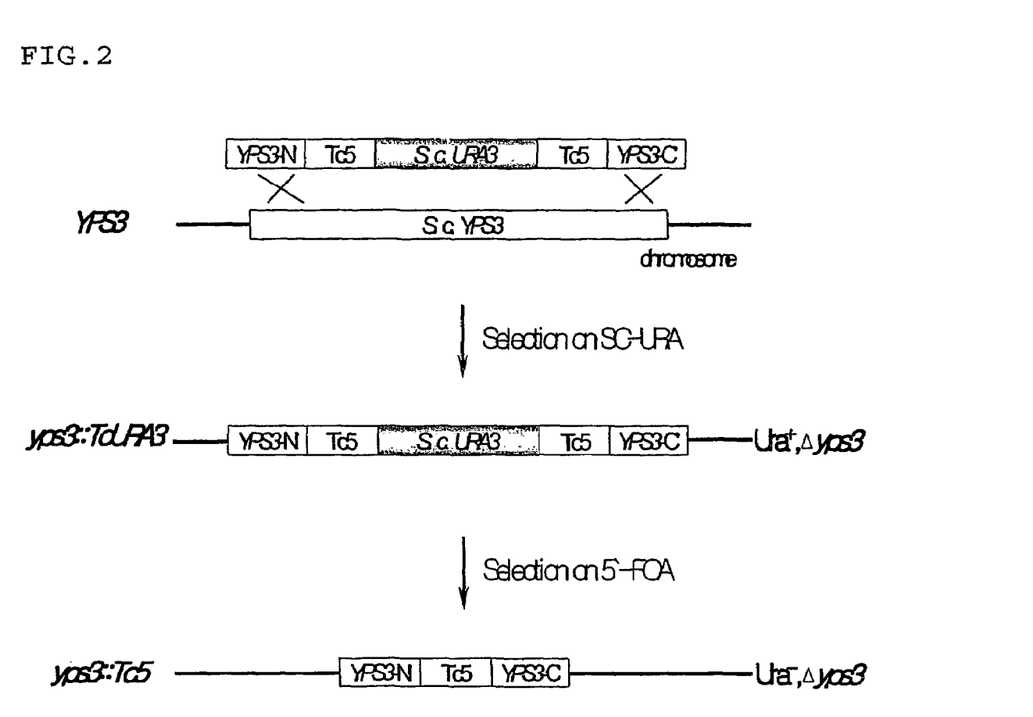
FIG. 2 is a diagram showing a process of disrupting the YPS3 gene of *Saccharomyces cerevisiae* and recovering the URA3 selection marker.

Next, the YPS3 gene of *Saccharomyces cerevisiae* was disrupted by use of the URA3 cassettes, followed by recovering the URA3 selection marker therefrom, as illustrated in FIG. 2.

In detail, after the DNA fragment obtained by the enzyme restriction treatment of the vector pB-yps3:: URA3: tc5 with EcoRI/XbaI was transfected into *Saccharomyces cerevisiae* strains 2805, L3262a, SLH11 (yps1Δ), SLH12 (yps2Δ), and SLH14 (ypsΔ/yps2Δ), primary selection for Ura⁺ transformants was made on SC-URA selection media. PCR was conducted to identify whether the Ura⁺ transformants were disrupted in the YPS3 gene, after which the yps3:: URA3: tc5 transformants thus selected were spread onto 5-FOA plates to select the yps3:: tc clones resulting from the pop-out of the URA 3 gene through homology recombination.

The disruption of the YPS3 gene in the finally obtained yps3Δ mutants was identified again by PCR to obtain yps3-disruptants, S28Y4, SLH15, SLH16, SLH17 and SLH18, which were optionally defective in other yapsin protease genes. These mutant stains are summarized in Table 2, below.

TABLE 2

Yps3-Deleted Yeast Strains

| Strain | Description/Genotype |
| --- | --- |
| S28Y4 | a yps3-disruptant of 2805<br>(MATα pep4::His3 prb-Δ1.6R can1 his3-20 ura3-52 yps3::tc5) |
| SLH15 | a yps3-disruptant of L3262<br>(MATa ura3-52 leu2-3, 112 his4-34 yps3::tc5) |
| SLH16 | a yps1/yps3-double disruptant of L3262<br>(MATa ura3-52 leu2-3, 112 his4-34 yps1::LEU2 yps3::tc5) |
| SLH17 | a yps2/yps3-double disruptant of L3262<br>(MATa ura3-52 leu2-3, 112 his4-34 yps2::HIS3 yps3::tc5) |
| SLH18 | a yps1/yps2/yps3-triple disruptant of L3262<br>(MATa ura3-52 leu2-3, 112 his4-34 yps1::LEU2 yps2::HIS4 yps3::tc5) |

EXAMPLE 2

Establishment of Recombinant Yeast Strain Expressive of hPTH and Analysis of hPTH Expression

*Saccharomyces cerevisiae* wild-type strain 2805 and L3262, and *Saccharomyces cerevisiae* mutants S28Y4, SLH15 (yps3Δ), SLH16 (yps1Δ/yps3Δ), SLH17 (yps2Δ/yps3Δ), and SLH18 (yps1Δ/yps2Δ/yps3Δ) were transformed with the expression vector pG10-hPTH1, followed by the selection of Ura⁺ transformants. These recombinant yeast strains capable of hPTH expression were subjected to hPTH expression analysis.

The yeast mutants were pre-cultured at 30° C. for 24 hours in minimal selective broths (amino acid-deficient yeast nitrogen substrate 0.67%, glucose 2%, casamino acid 0.5%). Each of the cultures was inoculated in an amount of 2% to a YPDG medium (yeast extract 1%, bacto peptone 2%, glucose 1%, galactose 1%) and then incubated at 30° C. for 48 hours. During this incubation, samples were withdrawn at 24 hours and 48 hours. 500 μl of each sample was centrifuged at 5,000 rpm for 5 min to separate a supernatant from biomass. DOC(deoxycholic acid) and TCA (trichloroacetic acid) each was added in the amount of one-tenth volume of the supernatant, which was then allowed to stand at 0° C. for 30 min to precipitate the proteins contained therein. Centrifugation dt 12,000 rpm for 10 min produced a pellet which was then washed with acetone to remove the TCA solution remaining in the precipitated protein, and dissolved in 25 μl of a lysis buffer, followed by heating at 100° C. for 5 min to obtain an extracellular protein fraction. 10 μl of the extracellular protein fraction was loaded on a 15% polyacrylamide separating gel (pH 8.8, 10 cm wide, 8 cm length, 0.7 mm thick) which was then subjected to electrophoresis at 125 V and 25 mA for 1.5 hours. The proteins run on the gel were visualized by Coumassie blue. The electrophoresis results are shown for the 24-hour sample in FIG. 3a and for the 48-hours sample in FIG. 3b.

Figure 3A:
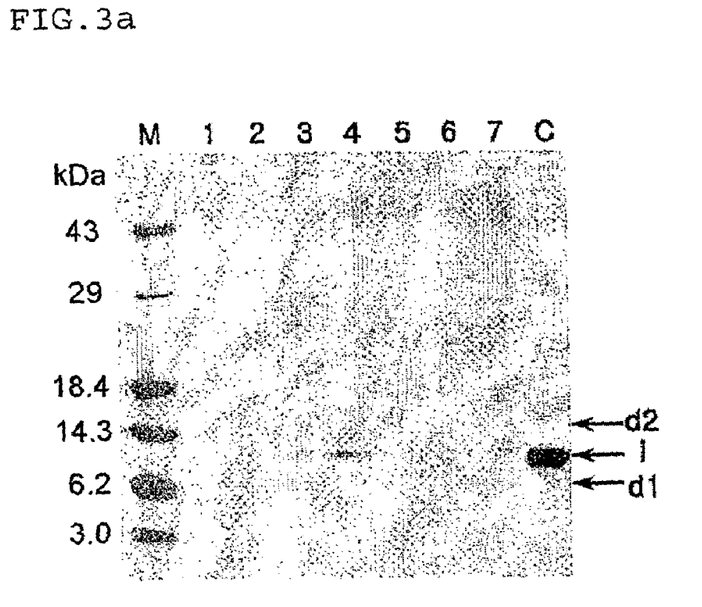
FIG. 3 shows SDS-PAGE results of hPTH molecules obtained from the cultures of *Saccharomyces cerevisiae* 2805 (lane 1), *Saccharomyces cerevisiae* 2805/pG10-hPTH1 (lanes 2 and 3), *Saccharomyces cerevisiae* SY28Y3/pG10-hPTH1 (lanes 4 and 5), and *Saccharomyces cerevisiae* SY28Y4/pG10-hPTH1 (lanes 6 and 7), along with 1 μg of native hPTH (C) and a prestained protein molecular weight marker (M) grown for 24 hours (a) and 48 hours (b), wherein band i stands for intact hPTH (1-84 a.a.), band d1 for a truncated hPTH (27-84 a.a.), and band d2 for hPTH (1-80 a.a.)
Figure 3B:
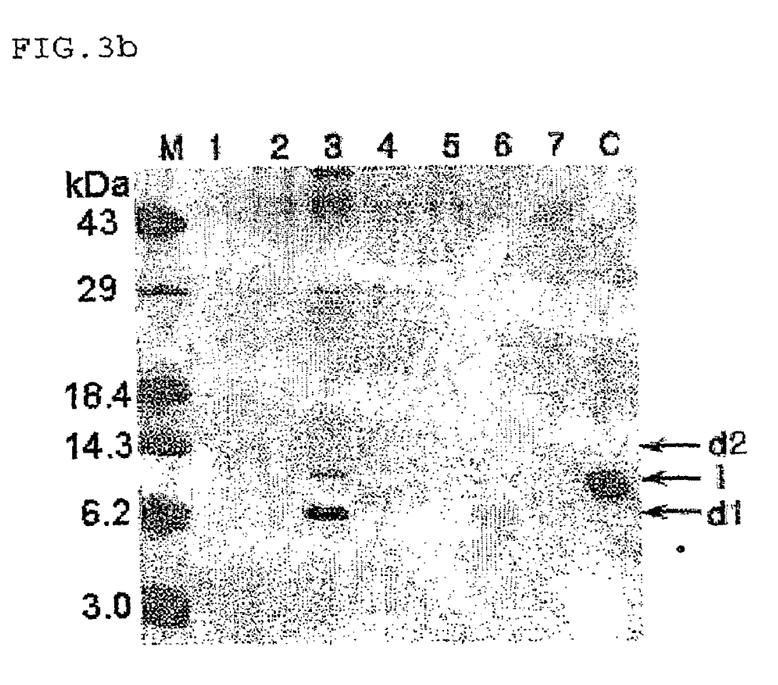

As seen in these electrophoresis photographs, the recombinant hPTH secreted from the *Saccharomyces cerevisiae* strains are separated on SDS-PAGE, appearing as three bands: i for the intact molecule (1-84);. d1 for an N-terminus truncated molecule (27-84); and d2 for a C-terminus truncated molecule (1-80). The proteins located in the i band and d1 band were transferred onto a PVDF (polyvinylidene difluoride) membrane. N-terminal amino acid sequencing of the proteins with the aid of MilligenlBiosearch M 600 protein sequencer identified the amino acid sequences Ser-Val-Ser-Glu-Ile (SEO ID NO: 5) and Lys-Leu-Gln-Asp-Val (SEQ ID NO: 6) at the N-terminal regions of the proteins of the i and d1 bands, respectively, indicating that the protein of the i band is the intact molecule of hPTH while the protein of the d1 band is a truncated form (27-84) which is lacking in 26 amino acid residues of the N-terminal region of hPTH. As for the d2 band, its protein, though showing an electrophoretic band of 14 kDa larger than the intact molecule, was found to be a truncated hPTH form lacking 4 to 5 amino acid residues of the C-terminus (1-79, 80) as analyzed by HPLC, MALDI mass spectrometry, and C-terminal amino acid sequencing. The characteristic electrophoretic pattern is reported to be attributed to the conformational change of the protein resulting from the removal of the C terminus (Vad et al., Protein Expr. Purif 13:396-402 (1998)).

EXAMPLE 3 hPTH Expression Patterns in Yapsin Protease-Deficient Mutants

To examine the effect of the disruption of YPS1 and YPS3 genes on hPTH expression, hPTH molecules secreted from the non-transformed, wild-type *Saccharomyces cerevisiae* 2805, the transformed wild-type *Saccharomyces* 2805/pG10-hPTH1, the transformed yps1Δ mutant S28Y3/pG10- hPTH1, and the transformed yps3Δ mutant S28Y4/pG10-hPTH1 were subjected to SDS-PAGE electrophoresis. The electrophoresis results are shown in FIG. 3.

As seen in the electrophoresis photographs, no hPTH-molecules were expressed in the non-transformed wild-type strain (lane 1). About 50% or more of the hPTH expressed in the transformed wild-type strain 2805 existed in the truncated d1 form (lanes 3 and 4). In the case of the yps1Δ mutant S28Y3, the truncated forms of the hPTH secreted into the media comprised 5% or less of the total hPTH when it was obtained from the 24-hour culture. In contrast, as much as about 30-40% of the hPTH obtained from the 48-hour culture was found to exist in the d1 form. The strain S28Y4, which was disrupted at YPS3 gene only, was not different from the wild type strain in hPTH expression patterns: about 50% or more of the hPTH secreted within 24 hours was found to exist in truncated forms.

The results, taken together and shown in FIG. 3 demonstrate that the main protease causative of the cleavage of hPTH in the early culture stage is Yapsin 1 and other proteases than Yapsin 1 are responsible for the cleavage of hPTH in the late culture stage. However, In the case of the strain that is disrupted at the YPS3 gene only, no significant effects can be obtained because the activity of Yapsin 1 already cleaves the hPTH to a significant extent in the early culture stage.

Figure 4A:
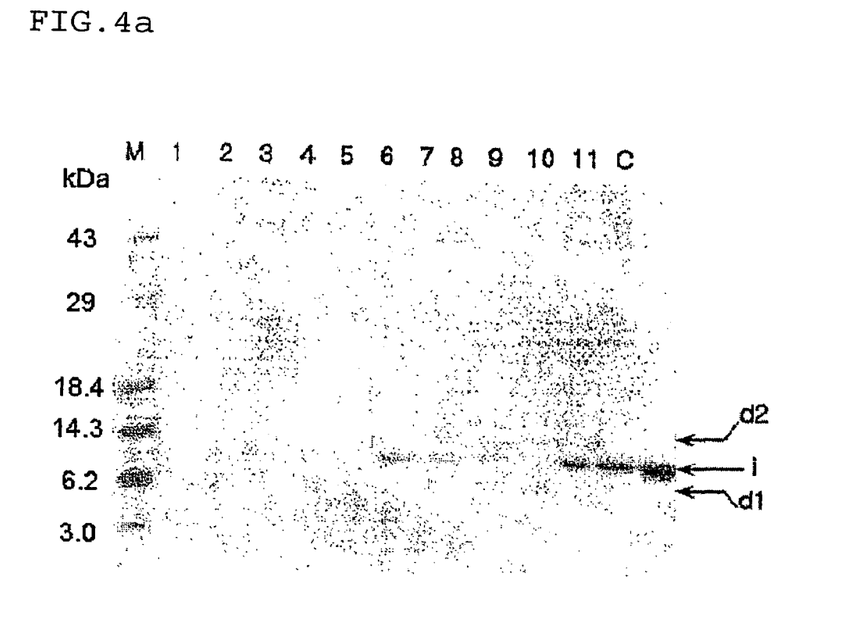
FIG. 4 shows SDS-PAGE results of hPTH molecules obtained from the cultures of *Saccharomyces cerevisiae* L3262 (lane 1), *Saccharomyces cerevisiae* L3262/pG10-hPTH1 (lanes 2 and 3), *Saccharomyces cerevisiae* SLH15/pG10-hPTH1 (lanes 4 and 5), *Saccharomyces cerevisiae* SLH16/pG10-hPTH1 (lanes 6 and 7), *Saccharomyces cerevisiae* SLH17/pG10-hPTH1 (lanes 9 and 9), and *Saccharomyces cerevisiae* SLH18/pG10-hPTH1 (lanes 10 and 11), along with 1 μg of native hPTH (C) and a prestained protein molecular weight marker (M) grown for 24 hours (a) and 48 hours (b), wherein band i stands for intact hPTH (1-84 a.a.), band d1 for a truncated hPTH (27-84 a.a.), and band d2 for hPTH (1-80 a.a.)
Figure 4B:
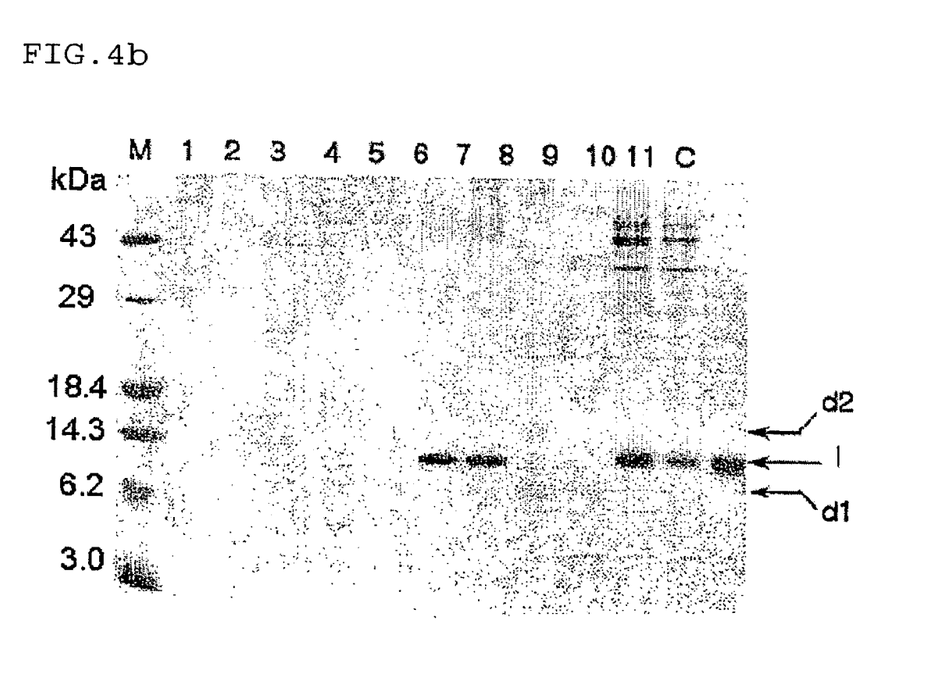

Accordingly, an examination was made of the expression pattern of hPTH production when the YPS3 gene was disrupted in combination with other Yapsin genes YPS1 and YPS2. To this end, hPTH was expressed in the non-transformed wild-type Saccharomyces cerevisiae L3262 serving as a control, the transformed L3262/pG10-hPTH1, the transformed yps3Δ mutant SLH15/pG10-hPTH1, the transformed yps1Δ/yps3Δ mutant SLH16/pG10-hPTH1, the transformed yps2Δ/yps3Δ mutant SLH17/pG10-hPTH1, and transformed yps1Δ/yps2Δ/yps2Δ mutant SLH18/pG10-hPTH1. Secreted proteins were electrophoresed in the same manner as above and the electrophoresis results are shown for the sample withdrawn after 24 hours of incubation in FIG. 4a and for the sample withdrawn after 48 hours of incubation in FIG. 4b.

As seen in FIG. 4, no hPTH was detected in the non-transformed strain (lane 1). As much as 50% of the hPTH secreted from the transformed wild-type strain (lanes 2 and 3), YPS3-disrupted strain (lanes 4 and 5), and YPS2 and YPS3-double disrupted strain (lane 6 and 7) existed in the N-terminus truncated d1 form when collected at 24 hours. After 48 hours, hPTH cleavage was found to be further aggravated to increase the proportion of truncated hPTH. On the other hand, interestingly, none of the hPTH molecules secreted from the YPS1 and YPS3-double disrupted strain (lanes 6 and 7) and YPS1, PYS2, YPS3-triple disrupted strain (lanes 10 and 11) had the N-terminus truncated d1 form even if they were obtained at 48 hours. In addition, it was revealed that the truncated form of d2 band comprised about 20% of the total hPTH secreted from the YPS1 and YPS3-double disrupted strain, while intact hPTH of the i band, but no d2 band protein, was observed even after 48 hours culture of the YPS1/YPS2/YPS3-triple disrupted strain. These results, taken together, showed that the hPTH degradation problem that the wild-type yeast strains have can be almost completely solved by use of the strain in which all of YPS1, YPS2 and YPS3 genes are disrupted.

EXAMPLE 4 hPTH Expression Patterns in High-Concentration Culture

An experiment was carried out to examine whether the hPTH expressed from the yapsin protease-deficient mutants created as above underwent proteolysis or not. In this regard, galactose was continually fed into the flask to imitate the conditions for high-concentration cultures in a fermentation bath. After pre-incubation for 24 hours in YPDG broths, the strains were further cultured for 72 hours while galactose was fed to the broths at intervals of 24 hours to maintain the galactose concentration of the broths at the level of 2%.

Under these conditions, hPTH was expressed in the non-transformed wild-type Saccharomyces cerevisiae L3262 serving as a control, the transformed L3262/pG10-hPTH1, the transformed yps1Δ mutant SLH11/pG10-hPTH1, the transformed yps1Δ/yps3Δ mutant SLH16/pG10-hPTH1, and transformed yps1Δ/yps2Δ/yps2Δ mutant SLH18/pG10-hPTH1. Secreted proteins were electrophoresed in the same manner as above and the electrophoresis results are shown for the strains L3262/pG10-hPTH1 and SLH11/pG10-hPTH1 in FIG. 5a and for the strains SLH16/pG10-hPTH1 and SLH18/pG10-hPTH1 in FIG. 5b.

Figure 5A:
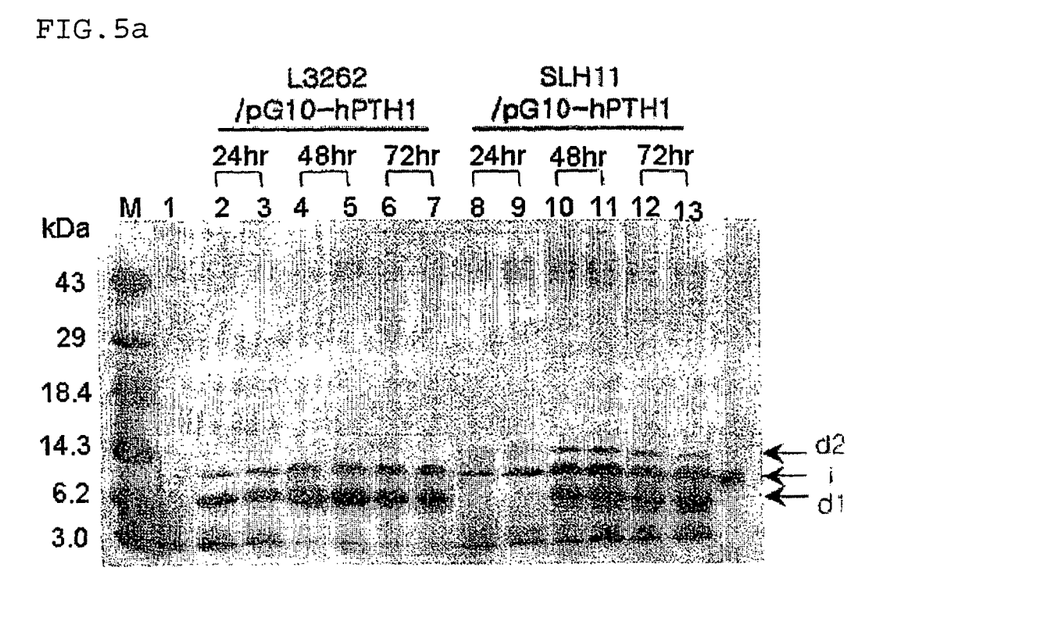
FIG. 5 shows SDS-PAGE results of hPTH molecules obtained from the cultures of *Saccharomyces cerevisiae* L3262 (lane 1), YPS1/YPS3-double disruptants of *Saccharomyces cerevisiae* L3262 (a): *Saccharomyces cerevisiae* L3262/pG10-hPTH1 (lanes 2 to 7) and *Saccharomyces cerevisiae* SLH11/pG10-hPTH1 (lanes 8 to 13), YPS1/YPS2/YPS3-triple disruptants (b) of *Saccharomyces cerevisiae* L3262: *Saccharomyces cerevisiae* SLH16/pG10-hPTH1 (lanes 2 to 7) and *Saccharomyces cerevisiae* SLH18/pG10-hPTH1 (lanes 8 to 13), along with 1 μg of native hPTH (C) and a prestained protein molecular weight marker (M) grown for 72 hours with continual supply of galactose, wherein band i stands for intact hPTH (1-84 a.a.), band d1 for a truncated hPTH (27-84 a.a.), and band d2 for hPTH (1-80 a.a.).
Figure 5B:
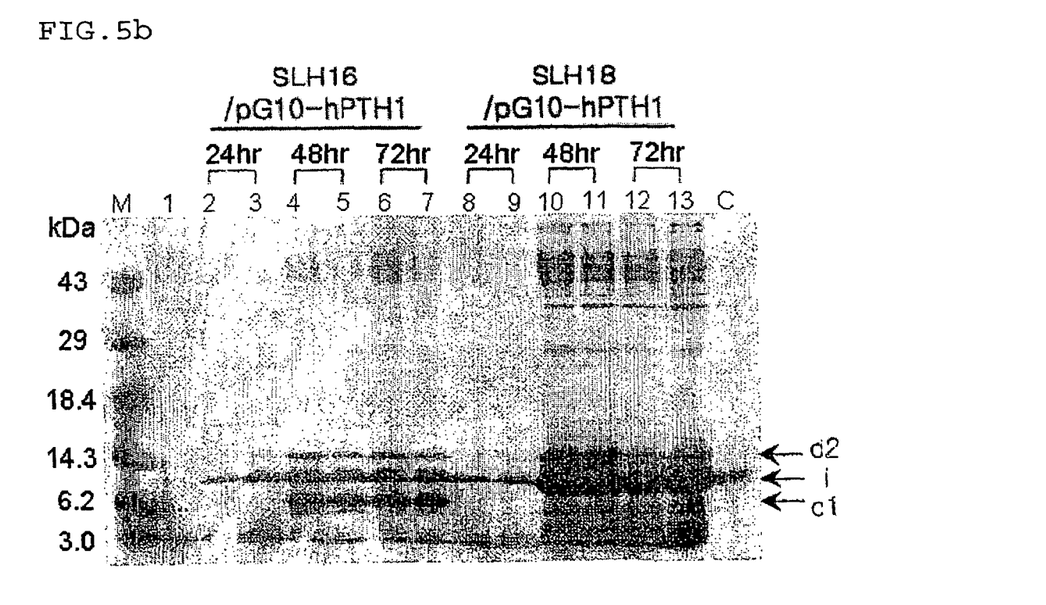

As seen in FIG. 5, as much as 50% of the hPTH secreted from the wild type yeast (lanes 2-7, FIG. 5a) already existed in the N-terminus truncated d1 form when collected at 24 hours. On the other hand, in the case of the cultures of the yps1Δ mutant (FIG. 5a, lanes 8-13) and the yps1Δ/yps3Δ mutant (lanes 2-7, FIG. 5b), hPTH was not degraded in the 24 hour cultures, while hPTH degradation was observed to be significant in the 48 hour high-concentration culture to which galactose had been provided continually. In contrast, the yps1Δyps2Δyps3Δ mutant cultures (lanes 8-13, FIG. 5b) were found to have no hPTH of the N-terminus truncated d1 form with significant increase of intact hPTH (i band) even when collected at 72 hours. Still even at 144 hours, the cultures of the triple-disrupted mutant were observed to have no truncated forms of hPTH. These results clearly demonstrated that the hPTH degradation problem which occurs in the late high-concentration culture stage can be completely solved by employing the mutant in which all of YPS1, YPS2 and YPS3 genes are disrupted.

As described hereinbefore, yeast mutants which are disrupted both in Yapsin 1 (previously YPA3) and Yapsin 3 genes (yps1Δ/yps3Δ) or all in Yapsin 1, Yapsin 2 (previously MKC7) and Yapsin3 genes (yps1Δ/yps2Δ/yps3Δ) can secrete intact hPTH, useful as therapeutics for various disorders, at high yield by virtue of their inability to degrade the hormonal peptide.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for producing a recombinant human parathyroid hormone (hPTH) from a *Saccharomyces cerevisiae* host, comprising the steps of:
   subjecting the *Saccharomyces cerevisiae* host to a deletion mutation in the genes encoding Yapsin 1 (YPS1) and Yapsin 3 (YPS3);
   transforming the *Saccharomyces cerevisiae* host with an expression vector containing a gene encoding human parathyroid hormone; and
   culturing the transformed *Saccharomyces cerevisiae* host in an appropriate medium.

2. The method as set forth in claim 1, wherein the deletion mutation is carried out by disrupting the genes encoding Yapsin 1 and Yapsin 3 by use of a *Saccharomyces cerevisiae* selection marker.

3. The method as set forth in claim 1, wherein the *Saccharomyces cerevisiae* host is further disrupted in the Yapsin 2 (YPS2) gene.

4. A *Saccharomyces cerevisiae* strain prepared by transforming a *Saccharomyces cerevisiae* yps1Δyps3Δmutant with an expression vector anchoring a human parathyroid hormone gene.

5. The *Saccharomyces cerevisiae* strain as set forth in claim 4, wherein the *Saccharomyces cerevzsiae* strain is *Saccharomyces cerevisiae* SLH16/pG10-hPTH (accession No. KCTC 0815BP) and the expression vector is pG10-hPTH1.

6. A *Saccharomyces cerevisiae* strain, prepared by transforming a *Saccharomyces cerevisiae* yps1Δyps2Δyps3Δ mutant with an expression vector anchoring a human parathyroid hormone gene.

7. The *Saccharomyces cerevisiae* strain as set forth in claim 6, wherein the *Saccharomyces cerevisiae* strain is *Saccharomyces cerevisiae* SLH18/pG10-hPTH (accession No. KCTC 0816BP) and the expression vector is pG10-hPTH1.

* * * * *

UNITED STATES PATENT AND TRADEMARK OFFICE
CERTIFICATE OF CORRECTION

PATENT NO. : 7,244,591 B2  Page 1 of 1
APPLICATION NO. : 10/363329
DATED : July 17, 2007
INVENTOR(S) : Sang Ki Rhee et al.

It is certified that error appears in the above-identified patent and that said Letters Patent is hereby corrected as shown below:

At column 1, at (*) Notice, under Number 73, please delete "This patent is subject to a terminal disclaimer."

At column 12, line 48, claim 4, please delete "3Δmutant" and insert -- 3Δ mutant --, therefor.

At column 12, line 52, claim 4, please delete "cerevzsiae" and insert -- cerevisiae --, therefor.

At column 12, line 57, claim 6, please delete "3A" and insert -- 3Δ --, therefor.

Signed and Sealed this

Twenty-fifth Day of December, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
gacgaattcc agaaacgtct gagtggag                28

<210> SEQ ID NO 2
<211> LENGTH: 27
<212> TYPE: DNA
<213> ORGANISM: Artificial Sequence
<220> FEATURE:
<223> OTHER INFORMATION: primer

<400> SEQUENCE: 2
gcaggatccg tactctaccg aatgccg                 27

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
cgcggatccc tatgcagacc agtgtgg                 27

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
cgctctagac tgcatgcaag gtctgac                 27